Figure 1:
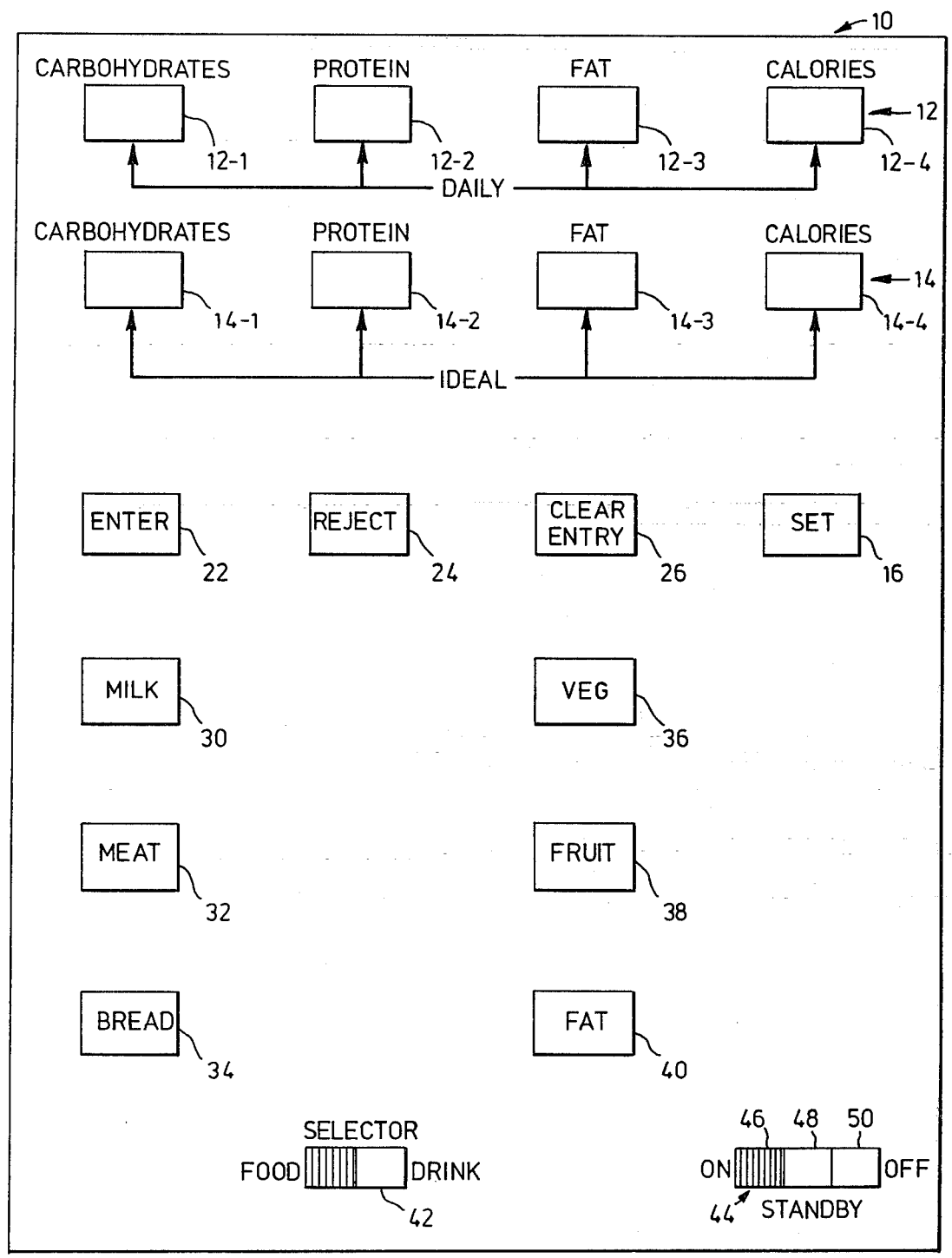

United States Patent [19]

Krames et al.

[11] 4,321,674
[45] Mar. 23, 1982

[54] NUTRITIONAL VALUE ACCUMULATING AND DISPLAY DEVICE

[76] Inventors: Lester Krames, 71 N. Oval, Hamilton, Ontario, Canada, L8S 3Y9; Kyong Kim, 1087 Parthia Crescent, Mississauga, Ontario, Canada, L5L 2L3

[21] Appl. No.: 159,976

[22] Filed: Jun. 16, 1980

[30] Foreign Application Priority Data

Jun. 20, 1979 [CA] Canada .................................... 330159

[51] Int. Cl.³ ............................................... G06F 15/42
[52] U.S. Cl. .................................... 364/413; 364/709; 364/715
[58] Field of Search ............... 364/413, 415, 705, 709, 364/715, 200, 900; 235/92 MT, 92 T

[56] References Cited

U.S. PATENT DOCUMENTS

| | | | |
|---|---|---|---|
| 4,095,274 | 6/1978 | Gordon | 364/413 |
| 4,101,071 | 7/1978 | Brejnik et al. | 235/92 MT |
| 4,212,079 | 7/1980 | Segar et al. | 364/415 |
| 4,244,020 | 1/1981 | Ratcliff | 364/413 |

OTHER PUBLICATIONS

"Electronic Diet Controller" by Moran, published in Computer Design, Aug. 1977, pp. 116–118.

*Primary Examiner*—Charles E. Atkinson
*Assistant Examiner*—Gary Chin
*Attorney, Agent, or Firm*—Rogers, Bereskin & Parr

[57] ABSTRACT

A device for accumulating and displaying nutritional values has first and second display units each of which displays carbohydrate, protein, fat and calorie values. Food items to be consumed are keyed into the device on a keyboard and the values assigned by the device to those items are displayed on the first display unit. When an entry key is pressed, the values for the newly entered items are added to the values of items previously entered for the day and the new totals are displayed in the first display unit. A desired daily calorie limit is selected by a selector button and the second display unit shows this limit and also the values assigned by a memory to that limit. If the calorie total in the first display unit exceeds the calorie limit displayed in the second display unit, an alarm is activated.

10 Claims, 2 Drawing Figures

NUTRITIONAL VALUE ACCUMULATING AND DISPLAY DEVICE

This invention relates to a device for accumulating and displaying nutritional values. The device is particularly intended to assist persons who are on diets, but the device may be used by any person who is concerned with proper nutrition.

At the present time persons who are on diets often carefully keep track of the total calories which they have received in a day. Such person often religiously analyze the number of calories in each item of food which consume in the day and maintain a running total, so that they can control their total calorie consumption during the day. This system does not take into account that different foods each having the same number of calories can supply very different nutritional values, and that one diet can be seriously deficient in required nutritional values while another diet having the same number of calories can provide adequate nutrition. Many dieters of course attempt to take nutritional factors into account when planning their diets, but the planning is usually carried out on a guess-work basis and requires more mental effort and discipline than most persons are able or willing to put forth.

Accordingly, it is an object of the present invention to provide a simple hand-held accumulating and display device into which food items can be entered, and which will accumulate and display nutritional values for these items over the course of a day. In its broadest aspect the invention provides a device for accumulating and displaying nutritional values comprising first and second display units, each having at least two display sections, namely a calorie display section and another food value display section, a keyboard for entering food items, control and memory means coupled to said keyboard for assigning a calorie value and said other food value to each food item keyed in on said keyboard, new entry storage means coupled to said control and memory means for receiving the calorie value and said other food value of a new food item keyed in on said keyboard, means connecting said first display unit with said new entry storage means and with said control and memory means for said first display unit to display the calorie value and said other food value of a food item keyed in on said keyboard, accumulator means coupled to said control and memory means, to said new entry storage means and to said first display means and operative to accumulate said values for a food item entered on said keyboard with the values of food items previously entered on said keyboard, to produce new total values of calories and said other food value, said keyboard including enter key means coupled to said accumulator means and to said control and memory means and operative to cause said new total values to be displayed in said first display unit, desired value storage means coupled to said second display unit and to said control and memory means for storing and for causing said second display unit to display a desired set of calorie and said other food value values, and comparison means coupled to said accumulator means and to said desired value storage means for comparing the calorie counts in each and for operating an alarm if the calorie count in said accumulator means exceeds the desired calorie count stored in said desired value storage means.

Figure 2:
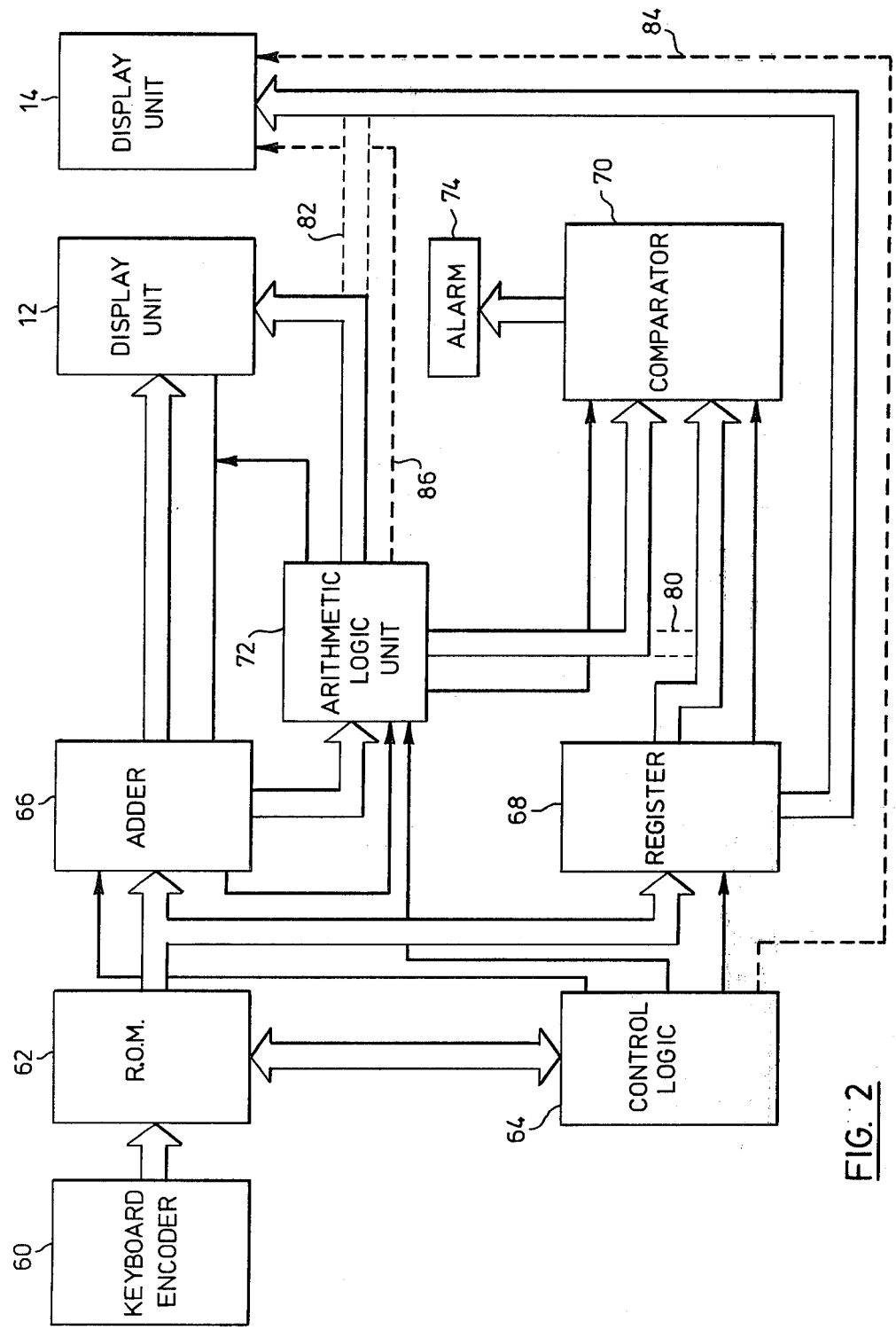

Further objects and advantages of the invention will appear from the following description, taken together with the accompanying drawings, in which:

FIG. 1 is a view of the face of a typical device according to the invention; and FIG. 2 is a block diagram of the circuit for the device of FIG. 1.

Reference is first made to FIG. 1, which shows a typical accumulating and display device 10 according to the invention. The device 10 includes two display units 12 and 14. Each display unit 12 is divided into four display sections, namely a carbohydrate display section 12-1, a protein display section 12-2, a fat display section 12-3, and a calorie display section 12-4. Display unit 14 is similarly divided into four corresponding display sections 14-1 to 14-4.

The device 10 also includes a keyboard having a calorie limit set button 16 to set the desired number of calories for the day, an enter key 22, a reject key 24, and a clear entry key 26. The keyboard also includes six category buttons 30 to 40 which are labeled respectively as milk, meat, bread, vegetable, fruit and fat. The device 10 further includes a selector switch 42 which has two positions, namely a food position and a drink position, as indicated. In addition, the keyboard includes a three position switch 44 having an "on" position 46, a "standby" position 48, and an "off" position 50.

The device 10 is based on the exchange diet principle, in which one gram of carbohydrate is considered to be the equivalent of four calories, one gram of protein is considered to be the equivalent of four calories, and one gram of fat is considered to be the equivalent of 9 calories. The device 10 is used as follows.

Firstly, the user will move switch 44 to its on position 46 and will then press the calorie limit set button 16 to set the calorie limit which the user wishes to consume in one day. The circuit, as will be explained, is arranged to begin displaying calories beginning at 1,000 calories in calorie display section 14-4 and then to increase the number of calories displayed in 100 calorie increments so long as button 16 remains pressed. The procedure is much like setting the time in a digital electronic clock radio. The calorie count increases by an increment of 100 approximately once each second, and when button 16 is released, the calorie limit last displayed will remain in view. If the user wishes to set for example a daily calorie limit of 1,500 calories, he will keep the set button 16 pushed until 1,500 is displayed in display unit 14-4, at which time he will release button 16. The device 10 will at the same time display in display unit 14 the ideal calorie, protein and fat values for the daily calorie limit selected, as will be explained.

Next, the user may enter diet information for the foods which he is considering eating by pressing the appropriate category buttons 30 to 40 inclusive. For example assume that the user is considering eating a salami sandwich consisting of two slices of bread and two slices of salami with mayonnaise and lettuce. For the two slices of bread he will press the bread button twice. For the two slices of salami the user will press the meat button twice and the fat button twice. For the mayonnaise the fat button will be pressed once. Lettuce is a free vegetable and no entry is required for this. In normal use a plastic card or the like will be supplied with the device to inform the reader which food button should be pressed for most foods which he will encounter in normal life.

When foods are being entered, the selector switch 42 will be in the food position. If the user is planning to consume a drink, the selector switch 42 will be moved to the drink position, at which time each of the buttons 30 to 40 will represent a different drink, for example soft drink, fruit juice, vegetable juice, wine, beer and liquor.

As information is keyed into the unit on category buttons 30 to 40, nutrition and calorie values will appear in the various display sections of display unit 12. Display unit 12 will display a running total of the information keyed in, so that when the entries for the salami sandwich are keyed in, the display in display unit 12 will appear as follows:

| When The User Presses | These Figures Will Appear | | | |
|---|---|---|---|---|
| | Carbohydrate Section 12-1 | Protein Section 12-2 | Fat Section 12-3 | Calorie Section 12-4 |
| Bread (one time) | 13 | 2 | 1 | 69 |
| Bread (second time) | 26 | 4 | 2 | 138 |
| Meat (one time) | 26 | 11 | 7 | 211 |
| Meat (second time) | 26 | 18 | 12 | 284 |
| Fat (one time) | 26 | 18 | 16 | 320 |
| Fat (second time) | 26 | 18 | 20 | 356 |
| Fat (third time) | 26 | 18 | 24 | 392 |

When the user has keyed in the values for the food items which he is considering consuming, he may decide, based on these values displayed in display unit 12, that he does not wish to eat the item. In that case he will press the clear entry key 26, thereby clearing the display unit 12.

However, if the user decides to proceed, then he will next press the enter key 22. The values in display unit 12 will then be added to the values of the nutrients already consumed in that day, and the new total, representing the new entry added to the previous consumption for the day, will be displayed in display unit 12.

The total values contained in display unit 12 are now compared with the ideal values which displayed in display unit 14 during the keying-in procedure and also when the enter key 22 is pressed. As discussed, calorie section 14-4 of display unit 14 will display the selected calorie limit for the day, as determined by calorie limiter button 16. The remaining sections of the display unit 14 display the ideal carbohydrate, protein and fat values for the selected calorie limit. The proportions of carbohydrates, protein and fat needed for any given daily calorie limit will of course vary as the daily calorie limit varies, and not necessarily in uniform proportion. Therefore, the ideal calorie, protein and fat values for each daily calorie limit selected are provided by a preprogramed memory, as will be described.

After the user presses the enter key 22 and the total values consumed for the day are displayed in display unit 12, then the total calories shown in display section 12-4 are compared not only by the user but also by the device 10 with the calorie limit for the day as displayed in display section 14-4. If the calories consumed, displayed in section 12-4, exceed the calorie limit for the day, displayed in section 14-4, then an alarm is triggered. The alarm is typically a beeping audible alarm but also may be a flashing light, indicated at 54 in FIG. 1.

If after the values for a food item have been entered, the user decides not to eat the food item, for example because the total calorie count for the day is too high, or because the fat content is too high in relation to the amounts of other nutrients, or for any other reason, then the user depresses the reject key 24. The values for that food item are then erased and the previous total for the day, without the values for the food item just entered, are then displayed in display unit 12. This turns off the alarm and the user can then consider an alternative food item. Since the user can see and judge whether any food will contribute suitably toward the desired allowances of carbohydrate, protein and fat for the day, as well as its calorie contribution, food selection is simplified.

FIG. 2 shows a block diagram for the device of FIG. 1. The block diagram is for a logic arrangement known as an R.O.M. or read-only memory oriented central processing unit or CPU, but other logic implementations may of course be used if desired. In FIG. 2 double arrow lines indicate data channels and single arrow lines present control channels.

As shown in FIG. 2, the keyboard buttons or keys, which are indicated in FIG. 1 as 16, and 22 to 44 inclusive, are collectively indicated as a keyboard encoder 60. Keyboard encoder 60 is connected to a read only memory or R.O.M. 62 which stores all of the programs necessary for the operation of the device and which is connected to a control logic block or CPU 64. The read-only memory 62 is connected to an adder 66 which is in turn connected to display unit 12. The read-only memory 62 is also connected to a register 68 which serves as a buffer and which is in turn connected both to display unit 14 and to a comparator 70. The adder 66 is also connected to an arithmetic logic unit 72, which serves as an accumulator, unit 72 being connected both to the comparator 70 and to the display unit 12.

An alarm indicated at 74 is connected to the comparator 70. The alarm 74 can be either the light 54 or an audible alarm circuit as described.

In operation, when the user selects a calorie limit for the day by operating button 16, this selects a specific program in read-only memory 62. The program selected provides the ideal carbohydrate, protein and fat values for the calorie limit selected. These values are stored in buffer register 68 and are also read at this time by control logic unit 64 from buffer register 68 into display unit 14.

Next, when the user enters a specific food item, for example the salami sandwich referred to previously, each item keyed in causes the control logic unit 64 to read the appropriate values from the read-only memory 62 into the adder 66. Adder 66 adds or accumulates the values keyed in at this time, and the contents of adder 66 are displayed in display unit 12. During the keying-in process, the user can compare the values which he is keying in with the ideal values selected for the day.

If the user decides to enter the food item keyed in, and presses the entry key 22, this causes the contents of adder 66 to be added to the accumulator in arithmetic logic unit 72. The contents of the accumulator in arithmetic logic unit 72 are now displayed in display unit 12 instead of the contents of adder 66. The user can now compare the consumed value for the day with the ideal values. In addition, the total calorie count contained in buffer register 68 and the total calorie count contained in the accumulator of arithmetic logic unit 72 are both fed to comparator 70 where they are compared. If the total calorie count in the accumulator of logic unit 72 exceeds that in buffer register 68, then comparator 70 activates the alarm 74.

If after the entry operation the user decides that he does not wish to eat the food item in question and presses the reject key 24, then the contents of adder 66 are subtracted from the contents of the accumulator in logic unit 72. The new values in the accumulator of logic unit 72 are then displayed in display unit 12, and if the total calorie count in the accumulator of unit 72 is less than that in buffer register 68, the alarm 74 is deactivated.

If the entry operation is completed and not rejected and then the user wishes to key in a new food item, then when he presses a category button to begin this procedure, the control logic unit 64, since the enter key 22 was last pressed, will clear the controls of adder 66 so that the new values may now be entered.

When the user has finished using the device 10 for a given meal during the day, he will move switch 44 from its on position 46 to its standby position 48. This causes the control logic unit 64 to turn off the displays in display units 12, 14 to save power, and also to clear any values in adder 66. The values entered thus far for the day, contained in the accumulator of arithmetic logic unit 72, are left in place, as are the ideal values set for the day and contained in buffer register 68. The circuits provided are, as is standard, such that the contents of the accumulator in arithmetic logic unit 72 and the contents of register 68 will remain undisturbed when the device 10 is off, so that data is not lost at this time.

When the user wishes to reset the device for a new day, he will move the switch 44 to the "off" position, which clears the accumulator in arithmetic logic unit 72 so that it can begin accumulating values for a new day. The contents of buffer register 68 are also then cleared so that a new calorie limit can be set for the next day.

If desired the logic can be arranged so that when a food item is keyed into the device, the values for the item are not only placed in register 56 and displayed in display unit 12, but are also at the same time added to the accumulator in arithmetic logic unit 62. Then when the enter key 22 is pressed, the values in the accumulator of unit 62 are displayed in display unit 12 and comparator 60 is operated. If the user dislikes the results, he then presses the reject key 24, which as before subtracts the values in register 56 from the accumulator in unit 62 and at the same time erases the contents of register 56. For this case the clear entry key 26 will not be needed since the reject key 24 effectively provides the same result. However the system previously described is preferred since with it, the user can change his mind about a food item at two times, namely while he is keying it in and after he has entered it, thus giving him more opportunities to reject a food item.

If desired, display unit 14 can be used during the keying-in procedure to display values "left to go" for the day. For example, if the daily calorie limit is set at 1600 calories and the user begins to key in the salami sandwich referred to previously then when he presses the first entry for bread (which has 69 calories), display unit 14-4 will display 1531 calories, indicating that he now has 1531 calories remaining for the day. This process continues as the components of a food item or meal are keyed in, but when the enter key 22 is pressed, the display in display unit 14 reverts back to the selected ideal values.

When this arrangement is used, arithmetic logic unit 72 will receive data from the register 68 via channel 80 shown in dotted lines in FIG. 2 and will also provide data to display unit 14 via data channel 82 also shown in dotted lines. A control channel 84 will extend from unit 72 to display unit 14 and another control channel 86 will extend from control logic unit 64 to display unit 14, as both shown in dotted lines.

Then, when values are keyed in and placed in adder 66, the combined contents of adder 66 and of the accumulator logic unit 72 are subtracted from the desired values in buffer register 68, and the results are displayed in display unit 14 as being the values "left to go" for the day. This process is repeated as new food items are keyed in. Then when the enter key 22 is operated, the control logic unit 64 causes the ideal values previously set to be read from buffer register 68 into the display unit 14, as before.

If desired, to save batteries, the ROM 62 can be arranged so that when the ideal values are set for the day, they will remain on only for a time delay of a few seconds after set button 10 is released. ROM 62 will then be programmed so that the ideal values will come on whenever the entry key 22 is pressed, and also during the keying-in procedure (unless the display unit 14 displays values "left to go" during the keying-in procedure).

Since the enter and reject keys 22, 24, the calorie limit set button 16, and the off position of switch 44 should not be operated inadvertently, they will all preferably be recessed switches which cannot easily mistakenly be operated.

If desired, the device 10 may be used to accumulate weekly instead of daily values, and may also be used to display only one value (such as carbohydrates) with the calorie display instead of displaying all three values of protein, fat and carbohydrate. The device 10 may also be used to display with calories a different selected value, e.g. one or more selected vitamins, minerals or cholesterol, instead of carbohydrate, protein and fats; such selected value will be programmed in the ROM 62 or may be a separate plug-in ROM.

What we claim as our invention is:

1. A device for accumulating and displaying nutritional values comprising:
   (a) first and second display units, each having at least two display sections, namely a calorie display section and another food value display section,
   (b) a keyboard for entering food items,
   (c) control and memory means coupled to said keyboard for assigning a calorie value and said other food value to each food item keyed in on said keyboard,
   (d) new entry storage means coupled to said control and memory means for receiving the calorie value and said other food value of a new food item keyed in on said keyboard,
   (e) means connecting said first display unit with said new entry storage means and with said control and memory means for said first display unit to display the calorie value and said other food value of a food item keyed in on said keyboard,
   (f) accumulator means coupled to said control and memory means, to said new entry storage means and to said first display means and operative to accumulate said values for a food item entered on said keyboard with the values of food items previously entered on said keyboard, to produce new total values of calories and said other food value, (g) said keyboard including enter key means coupled to said accumulator means and to said control and memory means and operative to cause said new total values to be displayed in said first display unit, (h) desired value storage means coupled to said second display unit and to said control and memory means for storing and for causing said second display unit to display a desired set of calorie and said other food value values;

(i) and comparison means coupled to said accumulator means and to said desired value storage means for comparing the calorie counts in each and for operating an alarm if the calorie count in said accumulator means exceeds the desired calorie count stored in said desired value storage means.

2. A device according to claim 1 wherein said other food value is selected from the group consisting of carbohydrate, protein and fat.

3. A device according to claim 1 wherein said first and second display units have four display sections, namely a carbohydrate display section, a protein display section, a fat display section and a calorie display section.

4. A device according to claim 1 including adjustable calorie limiter means coupled to said control and memory means for selecting from a desired calorie range a desired calorie total to be stored in said desired value storage means, said control and memory means including a stored program for assigning values of said other food value to selected calorie values in said desired calorie range.

5. A device for accumulating and displaying nutritional values comprising:

(a) first and second display units, each having four display sections, namely a carbohydrate display section, a protein display section, a fat display section and a calorie display section, (b) a keyboard for entering food items, (c) control and memory means coupled to said keyboard for assigning carbohydrate, protein, fat and calorie values to each food item keyed in on said keyboard, (d) new entry storage means coupled to said control and memory means for receiving the carbohydrate, protein, fat and calorie values of a new food item keyed in on said keyboard, (e) means connecting said first display unit with said new entry storage means and with said control and memory means for said first display unit to display the carbohydrate, protein, fat and calorie values of a food item keyed in on said keyboard, (f) accumulator means coupled to said control and memory means, to said new entry storage means and to said first display means and operative to accumulate said values for a food item entered on said keyboard with the values of food items previously entered on said keyboard, to produce new total values of carbohydrate, protein, fat and calories, (g) said keyboard including enter key means coupled to said accumulator means and to said control and memory means and operative to cause said new total values to be displayed in said first display unit, (h) desired value storage means coupled to said second display unit and to said control and memory means for storing and for causing said second display unit to display a desired set of carbohydrate, protein, fat and calorie values, (i) and comparison means coupled to said accumulator means and to said desired value storage means for comparing the calorie counts in each and for operating an alarm if the calorie count in said accumulator means exceeds the desired calorie count stored in said desired value storage means.

6. A device according to claim 5 including reject key means operatively coupled to said accumulator means for cancelling from the total values in said accumulator means the values contained in said new entry storage means.

7. A device according to claim 6 including adjustable calorie limiter means coupled to said control and memory means for selecting from a desired calorie range a desired calorie total to be stored in said desired value storage means, said control and memory means including a stored program for assigning desired carbohydrate, protein and fat values to selected calorie values in said desired calorie range.

8. A device according to claim 7 wherein said keyboard includes keys for entering milk, meat, bread, vegetable, fruit and fat food items.

9. A device according to claim 8 wherein said keyboard includes keys for entering drinks in addition to milk.

10. A device according to claim 5 wherein said control and memory means includes means responsive to operation of said enter key for operating said accumulator means to cause said values of a food item just entered on said keyboard to be accumulated with the values of food items previously entered on said keyboard.

* * * * *